United States Patent [19]

Bargar et al.

[11] Patent Number: 4,588,733

[45] Date of Patent: May 13, 1986

[54] 2-PHENYLPYRANO[2,3-B]PYRIDINES AND THEIR USE IN INHIBITING VIRUSES

[75] Inventors: Thomas M. Bargar, Zionsville; John K. Daniel, Indianapolis, both of Ind.

[73] Assignee: Merrell Dow Pharmaceuticals Inc., Cincinnati, Ohio

[21] Appl. No.: 663,020

[22] Filed: Oct. 19, 1984

[51] Int. Cl.$^4$ .................. A61K 31/44; C07D 491/052
[52] U.S. Cl. ..................................... 514/302; 546/115; 546/116
[58] Field of Search ................. 546/115, 116; 514/302

[56] References Cited

U.S. PATENT DOCUMENTS

| 3,518,273 | 6/1970 | von Strandtmann et al. | 546/115 |
| 4,371,537 | 2/1983 | Markley et al. | 546/294 |

FOREIGN PATENT DOCUMENTS

| 4579 | 10/1979 | European Pat. Off. . |
| 25599 | 3/1981 | European Pat. Off. . |
| 25598 | 3/1981 | European Pat. Off. . |
| 25600 | 3/1981 | European Pat. Off. . |

OTHER PUBLICATIONS

Bauer et al., Nature, vol. 292, pp. 369–370 (1981).
Sliwa, Bulletin de la Soc. Chimique de France, No. 2, pp. 631–641 (1970).

*Primary Examiner*—Henry R. Jiles
*Assistant Examiner*—Bernard I. Dentz
*Attorney, Agent, or Firm*—John J. Kolano

[57] ABSTRACT

2-Phenylpyrano[2,3-b]pyridines are described herein. These compounds are active against a variety of viruses. A number of procedures can be used to prepare the compounds of this invention but, at some point, they would all make use of the cyclization of a (phenyl) (pyridyl)propanol or (phenyl) (pyridyl)propenol.

16 Claims, No Drawings

2-PHENYLPYRANO[2,3-B]PYRIDINES AND THEIR USE IN INHIBITING VIRUSES

The present invention relates to pyrano[2,3-b]pyridines having a phenyl-substituent at the 2-position. More particularly, it relates to compounds having the following general formula:

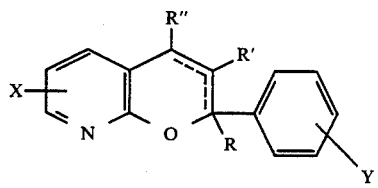

wherein R, R' and R" are each hydrogen or lower alkyl of 1–4 carbon atoms; X is hydrogen, chloro, bromo, alkylthio, alkylsulfinyl, alkylsulfonyl, hydroxy, alkoxy, benzoyl, acetyl or alkyl; Y is hydrogen, halo, di- or tri-chloro, alkyl, alkoxy, methylenedioxy, or phenoxy; and the dotted line indicates the optional presence of a double bond at the 2,3- or 3,4-positions, with the proviso that when the dotted line represents a double bond at the 2,3-position, then the R-group is not present.

Any reference to alkyl or lower alkyl groups above, either alone, as part of a larger group such as alkylthio or alkylsulfonyl, or implicitly as part of alkoxy(alkyloxy), covers compounds wherein the alkyl group contains 1 to 4 carbon atoms. Examples of such alkyl or alkyl-containing groups are methyl, ethyl, propyl, butyl, methylthio, ethylthio, butylthio, methylsulfinyl, ethylsulfinyl, butylsulfinyl, methylsulfonyl, ethylsulfonyl, butylsulfonyl, methoxy, ethoxy, propoxy and butoxy. The substituent X in the above structural formula can be located at any available position on the pyridine ring (i.e., at the 5, 6, or 7 positions in the pyrano[2,3-b]pyridine structure) although the 6-position of the pyrano[2,3-b]pyridine structure is preferred. The halo substituents referred to above in regard to Y include fluoro, chloro or bromo. The Y-group can also indicate poly substitution on the phenyl ring such as dichloro, trichloro or methylenedioxy. In the case of the dichloro or trichloro substitution, all isomers are included although the 4-chlorophenyl and 3,4-dichlorophenyl compounds are preferred. In the case where Y is methylenedioxy, that substituent is at the 3,4-position of the phenyl ring.

Examples of compounds encompassed by the present invention are the following:
2-(3,4-Dichlorophenyl)-3,4-dihydro-6-(methylsulfonyl)-2H-pyrano[2,3-b]pyridine.
6-Bromo-2-(3,4-dichlorophenyl)-3,4-dihydro-2H-pyrano[2,3-b]pyridine.
6-Bromo-2-(3,4-methylenedioxyphenyl)-3,4-dihydro-2H-pyrano[2,3-b]pyridine.
6-Bromo-2-(2,4-dichlorophenyl)-3,4-dihydro-2H-pyrano[2,3-b]pyridine.
2-(3,4-Dichlorophenyl)-3-methyl-3,4-dihydro-6-(methylsulfonyl)-2H-pyrano[2,3-b]pyridine.
2-(3,4-Dichlorophenyl)-4-methyl-3,4-dihydro-6-(methylsulfonyl)-2H-pyrano[2,3-b]pyridine.
2-(3,4,5-Trichlorophenyl)-3,4-dihydro-6-(methylsulfonyl)-2H-pyrano[2,3-b]pyridine.
2-(4-Methoxyphenyl)-3,4-dihydro-6-(methylsulfonyl)-2H-pyrano[2,3-b]pyridine.
2-(3,4-Dichlorophenyl)-3,4-dihydro-6-(n-butylsulfonyl)-2H-pyrano[2,3-b]pyridine.
2-(3,4-Dichlorophenyl)-3,4-dihydro-6-acetyl-2H-pyrano[2,3-b]pyridine.
2-(3,4-Dichlorophenyl)-3,4-dihydro-6-methoxy-2H-pyrano[2,3-b]pyridine.
7-Chloro-2-(3,4-dichlorophenyl)-3,4-dihydro-2H-pyrano[2,3-b]pyridine.

Certain preferences have already been indicated in defining the substituent groups above. In addition to and apart from those preferences are the ones given below. Those compounds wherein R, R' and R" are hydrogen are preferred compounds of the present invention. Another preferred group are those compounds wherein X and Y are other than hydrogen. A further preferred group are those compounds wherein X and Y are other than hydrogen while R, R' and R" are each hydrogen. A further preferred group of compounds are those wherein X is chlorine, bromine or methysulfonyl at the 6-position of the pyranopyridine structure. A still further preferred group of compounds are those wherein Y is 4-chloro or 3,4-dichloro.

The pyranopyridines of the present invention are obtained by the cyclization of appropriate alcohols of the following structural formulas

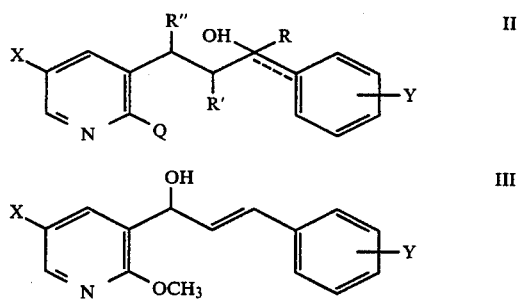

wherein X, Y, R, R' and R" are defined as above and Q is methoxy or chlorine. When a 2-methoxypyridine is involved, the indicated compound is first reacted with hydrobromic acid to cleave the ether and the cleavage product is immediately reacted with an acid such as acetic acid to bring about cyclization to give the pyranopyridine. When Q is chlorine, the alcohol is subjected to strong base to bring about cyclization. In the case of starting material III, the allylic alcohol involved must first isomerize to an allyl ion analogous to that obtained from structure II before cyclization will take place. In those instances where the intermediate alcohol is obtained from the corresponding ketone by reduction, it is generally more convenient to carry out the reduction to give the alcohol and then immediately cyclize the alcohol as indicated without specifically isolating it. Nevertheless, the alcohol is obtained in the process and it could be isolated in a pure form and cyclized in a step-wise fashion if desired.

Where the final product obtained above contains unsaturation at the 3,4-position of the pyranopyridine ring, it can be reduced catalytically with hydrogen and Raney nickel to give the corresponding 3,4-dihydro compound or the double bond can be isomerized to the 2,3-position by means of a base such as 1,8-diazabicyclo[5.4.0]undec-7-ene.

The cyclization procedure already described is used at some point in the preparation of the compounds of the present invention. Several methods are available for obtaining the alcohol used as the starting materials and these can be summarized in the following schemes:

SCHEME I

To obtain the compounds corresponding to III above, an appropriate cinnamaldehyde is reacted with a lithium compound of the formula

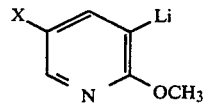

in an inert solvent by standard procedures. The indicated lithium compound is ordinarily prepared in situ from the corresponding 3-bromopyridine using reagents such as n-butyllithium in ether at −70° C. The indicated bromo compound is itself obtained by bromination of the appropriate 2-methoxy-5-X-pyridine in acetic acid.

SCHEME II

The lithium compound (IV) referred to in scheme I can also be used to prepare other alcohol intermediates of type II wherein Q is methoxy. Specifically, lithium compound IV is reacted with dimethylformamide to replace the lithium with a formyl group. The resulting pyridine-3-carboxaldehyde is then condensed with an appropriate acetophenone in the presence of a strong base in a Claisen-Schmidt condensation to give a chalcone. The carbonyl group of the chalcone is then reduced by means of a reagent such as sodium borohydride to give an alcohol of the general type shown by formula II above.

Alternatively, the olefinic double bond of the chalcone could be reduced first by means of hydrogen and Raney nickel followed by reduction of the carbonyl group as described. This would give a saturated alcohol which would then be cyclized to give the 3,4-dihydropyranopyridine.

In a variation on this chalcone procedure, the lithium compound IV can be reacted with acetonitrile or with acetaldehyde followed by oxidation to give the corresponding 3-acetylpyridine. This acetylpyridine is then reacted with an appropriate substituted aldehyde in a Claisen-Schmidt condensation to give a chalcone as described earlier although it would be an isomeric ("reverse") chalcone. That is, reduction of the carbonyl group of the chalcone would give an alcohol of type III which would be similar to that obtained according to scheme I discussed earlier.

SCHEME III

In another approach to the preparation of the intermediate alcohols referred to earlier, the 3-bromo compound which had been used to prepare lithium compound IV can be used in a Heck reaction. That is, the bromopyridine is reacted with an ethenyl alcohol of the formula

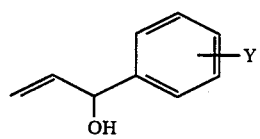

in the presence of palladium diacetate and an inert solvent to give a ketone of the formula

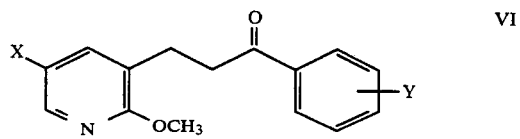

The carbonyl group of the ketone is then reduced to an alcohol of type II described earlier using standard agents such as sodium borohydride. The indicated ketone VI can also be reacted with an alkyl Grignard reagent (RMgCl) to give the corresponding tertiary alcohol. Such a procedure would be used to prepare those compounds wherein R is alkyl.

SCHEME IV

In what could be considered as a variation of scheme III, a Heck reaction could be carried out using ethenyl alcohol V and 2-chloro-3-iodo-5-(methylsulfonyl)pyridine to give a ketone analogous to VI except that the methoxy group is replaced by a 2-chloro. This ketone would then be reduced to the corresponding alcohol using diisobutylaluminum hydride at low temperature and the resulting alcohol would be cyclized as described earlier for 2-chloropyridines. The necessary iodo compound used in this procedure can be obtained by starting with 2,5-bis(methylsulfonyl)pyridine and treating it with sulfuric acid to hydrolyze the 2-substituent followed by iodination with potassium iodide/potassium iodate with the procedure giving 3-iodo-5-(methylsulfonyl)-2(1H)-pyridinone as the product. This is then treated with phosphorus oxychloride to give the corresponding 2-chloropyridine. The corresponding compound containing bromide in place of iodine can be obtained by using a brominating agent instead of an iodinating agent in the procedure described above followed by conversion to the 2-chloro compound. The resulting 3-bromo compound could be used in the same way as the 3-iodo compound.

In addition to the general procedure described earlier, certain of the final products described above can also be used to prepare other products. Specifically, the final product wherein X is 6-bromo can be reacted with an alkyl lithium such as t-butyllithium at −100° C. to give the corresponding 6-lithio derivative. This lithio derivative can be reacted in situ to give a variety of other 6-substituted products. Thus, reaction of the lithium compound with a dialkyl disulfide gives the corresponding 6-alkylthio compound. This alkylthio compound can then be oxidized to the corresponding alkylsulfinyl and alkylsulfonyl compounds using the appropriate oxidizing agent.

Reaction of the lithio compound with benzonitrile or acetonitrile would give the corresponding 6-benzoyl or 6-acetyl compound. Alternatively, the lithium compound can be reacted with acetaldehyde to give the corresponding alcohol followed by oxidation of that alcohol to give the corresponding acetyl compound. To obtain the 6-alkyl compound, the lithium compound would be reacted with an alkyl halide such as methyl iodide.

In other procedures, the lithium compound can simply be quenched with methanol to give the corresponding 6-hydrogen compound. In yet another reaction, the lithium compound can be reacted with butyl borate followed by treatment with an oxidizing agent such as peroxide to give the corresponding hydroxy compound. Reaction of the hydroxy compound with dimethyl sulfate under alkaline conditions would then give the corresponding 6-methoxy compounds.

The procedures for the preparation of the compounds of this invention were described generally above only for the preparation of the 6-substituted compounds because that type of substitution is obtained most readily. However, similar procedures could be used for the preparation of isomeric compounds wherein the substituent is located at other positions on the pyridine ring. But, certain special procedures may be better for obtaining such isomeric compounds. Thus, it would be possible to start with 2-chloro-6-methoxypyridine and subject it to the series of reactions described in Schemes I or II to give a 6-bromo-7-chloro final product and then selectively remove the 6-bromo atom by catalytic hydrogenation. Alternatively, a 6-bromo final product could be lithiated at the 5-position followed by the introduction of various groups at that position by standard procedures eventually followed by removal of the 6-bromo atoms.

The compounds of the present invention are useful as antiviral agents. Thus, the compounds disclosed herein, that is, the antiviral compounds of formula I, can be used to inhibit viral replication by contacting a virus and preferably, virus host cells with an effective amount of the appropriate subject compound. The present invention is further directed to methods of using the compounds of the invention as antiviral agents in which a virus or virus host cell (i.e., a cell susceptible to infection by the virus) is contacted with an effective amount of one or more of the subject compounds. The present invention is also directed to antiviral compositions which can contain from about 0.00001% or less to about 99% by weight of the active compound in combination with a pharmaceutically acceptable carrier. Typically, in those combinations employing a low percentage of active compound, the pharmaceutically acceptable carrier is in liquid form, therefore a composition containing 0.00001% or less by weight of active compound is equivalent to a composition containing about 0.1 $\mu$g or less of the active compound per ml of carrier.

The antiviral compounds of the invention have been found to be particularly effective against picornaviruses, i.e., the small ribunocleic acid viruses. The picornaviruses include viruses such as Enteroviruses, Rhinoviruses and a number of plant disease viruses. There is some compound-to-compound variation in antiviral potency and spectrum of antiviral activity, and in toxicity and side effects.

Anvirial activity for the subject compounds was demonstrated utilizing the following tissue culture testing procedure.

HeLa cells (GIBCO, Grand Island, New York) were grown and maintained at 36° C. in Corning 75 cm$^2$ tissue culture flasks using Eagles Minimum Essential Medium with Earles Salts supplemented with 1% antibiotic stock solution. Seven to 10% heat inactivated fetal calf serum was added to the medium for cell growth (growth medium) and the concentration was reduced to 1% to 2% for cell maintenance (maintenance medium). Cell stocks were maintained in liquid nitrogen and utilized between passage levels 10 and 100.

HeLa cells were transferred to 24-well microtiter plates at a concentration of 1.0 to 1.3 $\times$ 10$^5$ cells per well in 1.0 ml growth medium. After 24 hours growth at 36° C. in a humidified CO$_2$ (5% CO$_2$, 95% air) incubator, the cultures were 60–75% monolayered and ready for use. Two mg of each test compound were mixed with 0.1 ml of acetone followed by addition of 10 ml of maintenance medium to give a stock concentration of 200 $\mu$g compound/ml. Dilutions were then prepared in the same medium to give the various test concentrations. HeLa cell cultures in the 24-well microtiter plates were drained and refed with 1.0 ml of compound-containing or compound-free maintenance medium. Appropriate monolayers were then challenged with 0.1 ml (10–100 TCID$_{50}$) virus. Cell cultures were incubated at 33° or 36° C. in the humidified CO$_2$ incubator and examined microscopically at 48, 72 and 96 hours after challenge for compound cytotoxicity and viral cytopathic effect (CPE). Viral CPE was graded as: —(no CPE); +1 (20% CPE); +2 (40% CPE); +3 (60% CPE); +4 (80% CPE); or +5 (100% CPE). The lowest concentration of compound reducing viral CPE by 50% or more compared to control was considered the minimum inhibitory concentration (MIC$_{50}$) of that compound.

Using the above procedure, the compounds of the present invention were tested against the viruses RV-1A, RV-2, RV-9, RV-39 and RV-64. As indicated earlier, variations in activity were observed but most of the compounds were active against all of the viruses with an MIC$_{50}$ of 1.3 $\mu$g/ml or less. Exceptions in this regard are 6-(butylthio)-2-(3,4-dichlorophenyl)-3,4-dihydro-2H-pyrano[2,3-b]pyridine (active only against RV-2 and RV-39); 3,4-dihydro-6-(methylsulfonyl)-2-phenyl-2H-pyrano[2,3-b]pyridine (active only against RV-2, RV-9 and RV-39 at 2.5, 2.5 and 5 $\mu$g/ml respectively); and 6-bromo-2-phenyl-2H-pyrano[2,3-b]pyridine (active only against RV-1A).

Some of the most active compounds in the above procedure were also tested against other virus and were found active against RV-1B, RV-10, RV-13, RV-21, RV-29, RV-32, RV-33, RV-44, RV-49, RV-55, RV-74, RV-89, RV-Hanks, Echo 6, Echo 12, Echo 30 and Entero 70 viruses.

Compounds of the present invention were also tested in mice (400 mg/kg, p.o.) and the mice sera were examined and significant quantities of test compound were found to be present.

Because of their distinct advantages (for example, broad spectrum antiviral activity at low compound concentration), the compounds 2-(3,4-dichlorophenyl)-3,4-dihydro-6-(methylsulfonyl)-2H-pyrano[2,3-b]pyridine, 6-bromo-2-(3,4-dichlorophenyl)-3,4-dihydro-2H-pyrano[2,3-b]pyridine and 6-chloro-2-(3,4-dichlorophenyl)-3,4-dihydro-2H-pyrano[2,3-b]pyridine are preferred embodiments of the present invention.

In using the subject compounds, a virus or virus host cell is contacted with an amount of one or more of the compounds effective to inhibit the virus. Although the invention should not be construed as limited to any particular theory of action, it appears that the compounds act to inhibit virus in host cells, rather than by direct chemical or physical inactivation of the virus particle apart from the cell. In antiviral applications carried out in non-living environments, contacting should be carried out in a manner which ensures continued presence of an effective amount of the compound when subsequent contact with host cells occurs. Preferably, the compounds are used by contacting the host cells with an effective antiviral amount (i.e., the amount which must be employed to achieve significant viral inhibition) of one or more of the compounds. The contacting can be carried out directly, as by addition of the compound to cells in tissue culture, to inhibit contaminating picornaviruses. Contacting can also be carried out by administering an anvirial dosage of a compound of the invention to an animal (preferably a mammal). The compounds can be administered to animals parenterally (for example, by intraperitoneal, subcutaneous or intravenous injection), topically (for example, used in an aerosol or skin lotion, or administered intranasally or buccally), rectally or orally. In such applications, an effective antiviral dose of one or more of the compounds is administered to an animal. Selection of the compound or compounds for administration to animals in particular cases is dictated by considerations such as toxicity, mutagenicity, ease of administration, antiviral activity (potency), stability, compatibility with suitable carriers, etc.

The exact amount of the compound or compounds to be employed, i.e., the amount of the subject compound or compounds sufficient to provide the desired effect, depends on various factors such as the compound employed; type of contacting or administration; the size, age and species of animal; the route, time and frequency of administration; the virus or viruses involved, and whether or not the compound is administered prophylactically or is administered to an infected animal to inhibit the infecting virus. In particular cases, the amount to be administered can be ascertained by conventional range finding techniques, for example, by observing the effect produced at different rates using conventional virus assay procedures.

The compounds are preferably administered in the form of a composition comprising the compound in admixture with a pharmaceutically-acceptable carrier, i.e., a carrier which is chemically inert to the active compound and which has no detrimental side effects or toxicity under the conditions of use. As indicated above, the compounds when administered to tissue culture medium exhibit significant antiviral activity at low concentrations, such as, for example, the 0.008 μg/ml of 6-bromo-2-(3,4-dichlorophenyl)dihydro-2H-pyrano[2,3-b]pyridine which caused a 50% reduction in cytopathic effect in testing against test virus RV-1A.

Such compositions can contain from about 0.1 μg or less of the active compound per ml of carrier to about 99% by weight of the active compound in combination with a pharmaceutically-acceptable carrier.

Preferred compositions include compositions containing from about 0.1 μg of active compound per ml of carrier to about 0.0025% to about 0.05% to about 0.25% to about 0.5% to about 1% to about 10% to about 25% to about 50% by weight of active compound in a pharmaceutically acceptable carrier.

The compositions can be in solid forms such as tablets, capsules, granulations, feed mixes, feed supplements and concentrates, powders, granules or the like; as well as liquid forms such as sterile injectable suspensions, orally administered suspensions or solutions. The pharmaceutically acceptable carriers can include excipients such as surface active dispersing agents, suspending agents, tableting binders, lubricants, flavors and colorants. Suitable excipients are disclosed, for example, in texts such as *Remington's Pharmaceutical Manufacturing*, 13th Edition, Mack Publishing Co., Easton, Pa. (1965).

The following examples are presented to illustrate the present invention but they should not be construed as limiting it in any way.

EXAMPLE 1

To a stirred suspension of 14.8 g of 2,5-dichloropyridine in 50 ml of methanol was added 30 ml of a 25% solution of sodium methoxide in methanol and the mixture was heated to reflux under nitrogen. After 24 hours, another 30 ml of the sodium methoxide solution was added and reflux was continued for a total of 68 hours. The sodium chloride which precipitated was removed by filtration and the filtrate was concentrated at atmospheric pressure to about ¼ the original volume and partitioned between ether and water. The aqueous layer was extracted with ether and the combined ether layers were washed with saturated sodium chloride solution, dried over potassium carbonate and concentrated at atmospheric pressure to a pale brown oil. This residue was distilled to give 5-chloro-2-methoxypyridine as a colorless liquid boiling at about 82°–84° C. at 20 torr.

When the above procedure was repeated using 2,5-dibromomopyridine, the product obtained was 5-bromo-2-methoxypyridine boiling at about 99°–101° C. at 28 torr.

EXAMPLE 2

To a stirred suspension of 2.5 g of anhydrous sodium acetate in 10 ml of acetic acid was added 4.3 g of 5-chloro-2-methoxypyridine followed by a solution of 3.1 ml of bromine in 10 ml of acetic acid. The mixture was warmed to 80° C. for 6 hours and then allowed to cool and stirred at 23° C. for 64 hours. It was then partitioned between ether and water and the resulting ether layer was washed with aqueous 1N sodium hydroxide solution and then with aqueous 5% sodium bisulfite solution, dried over potassium carbonate and concentrated at reduced pressure to leave a residual brown solid. This residue was bulb-to-bulb distilled with the material distilling at 140°–150° C. at 20 torr collected to give 3-bromo-5-chloro-2-methoxypyridine as a solid melting at about 45°–47.5° C.

EXAMPLE 3

To a stirred solution of 111.4 g of 2-methoxypyridine in 500 ml of acetic acid was added 164.1 g of anhydrous sodium acetate in portions over a period of about 5 minutes so as to avoid formation of lumps. Then, 179.3 ml of bromine was added at a rate so that the temperature remained below 35° C. After this addition, the mixture was warmed to 80° C. for 6 hours and then stirred at 25° C. for 16 hours. This mixture was poured into 2 liters of water and the resulting aqueous mixture was extracted with two 500-ml portions of carbon tetrachloride. The organic extract was washed with aqueous 1N sodium hydroxide, aqueous 1N sodium bisulfite, dried over magnesium sulfate, filtered and concentrated under reduced pressure to leave a yellow liquid which solidified on cooling. The crude product was distilled through a short Vigreux column at 3 torr and, after a fore-run consisting mainly of 5-bromo-2-methoxypyridine, the fraction boiling at 110°–112° C. at 3 torr was collected. This gave 3,5-dibromo-2-methoxypyridine as a white solid melting at about 49°–51° C.

EXAMPLE 4

A solution of 4.0 g of 3-bromo-5-chloro-2-methoxypyridine in 75 ml of anhydrous ether was cooled to −70° C. under nitrogen. The resulting slurry was stirred rapidly and there was added 12.0 ml of 1.65M n-butyllithium/hexane dropwise over a period of about 5 minutes while keeping the temperature below −70° C. The reaction mixture became homogeneous and, after 15 minutes, a solution of 3.0 g of 4-chlorocinnamaldehyde in 35 ml of ether was added dropwise while keeping the temperature below −60° C. The cold mixture was then poured into aqueous saturated sodium bicarbonate solution and the resulting mixture was extracted with ether. The ether layer was washed with aqueous saturated sodium chloride solution, dried over potassium carbonate and concentrated under reduced pressure to give a white solid. This solid was recrystallized from a mixture of ethyl acetate/hexane to give (E)-5-chloro-α-[2-(4-chlorophenyl)ethenyl]-2-methoxy-3-pyridinemethanol as white needles melting at about 135°-139.5° C.

When the above procedure was repeated using 3-bromo-5-chloro-2-methoxypyridine and 3,4-dichlorocinnamaldehyde, the product obtained was (E)-5-chloro-α-[2-(3,4-dichlorophenyl)ethenyl]-2-methoxy-3-pyridinemethanol.

EXAMPLE 5

A solution of 60.6 g of 3,5-dibromo-2-methoxypyridine in 900 ml of anhydrous ether was stirred under nitrogen and cooled to −78° C. to give a thick slurry. Efficient stirring was used to prevent the solid starting material from adhering to the wall of the reaction vessel. While the temperature was maintained below −65° C., 85 ml of 2.67M n-butyllithium/hexane was added dropwise. The reaction mixture was homogeneous upon completion of the addition and it was stirred for 15 minutes at −78° C. Then, a solution of 45.6 g of 3,4-dichlorocinnamaldehyde in 200 ml of anhydrous tetrahydrofuran was added dropwise while keeping the temperature below −65° C. When the addition was complete, 100 ml of aqueous saturated sodium bicarbonate solution was added to the cold reaction mixture. It was then allowed to warm to about −40° C. and then partitioned between ether and aqueous saturated sodium bicarbonate solution. The aqueous layer was extracted with ether and the combined ether layers were washed with aqueous saturated sodium chloride solution, dried over potassium carbonate, filtered and concentrated to leave a pale yellow solid. This was recrystallized from a mixture of 2-propanol/ethyl acetate/hexane (1:3:5) to give (E)-5-bromo-α-[2-(3,4-dichlorophenyl)ethenyl]-2-methoxy-3-pyridinemethanol melting at about 149°-150° C.

When the above procedure was repeated using 3,5-dibromo-2-methoxypyridine and cinnamaldehyde, the product obtained was (E)-5-bromo-α-(2-phenylethenyl)-2-methoxy-3-pyridinemethanol.

EXAMPLE 6

To a stirred suspension of 13.4 g of 3,5-dibromo-2-methoxypyridine in 200 ml of anhydrous ether at −70° C. under nitrogen was added dropwise 29.2 ml of 1.71M n-butyllithium/hexane over a period of about 20 minutes while keeping the temperature below −70° C. Stirring was continued for 10 minutes and then a solution of 7.7 ml of dimethylformamide in 10 ml of ether was added. The temperature rose to −55° C. and the mixture was allowed to cool again to −70° C. Then, after 15 minutes, the cold mixture was poured into excess aqueous 1M hydrochloric acid. The mixture was agitated until it came to room temperature, the layers were then separated and the aqueous layer was extracted with ether. The combined ether layers were washed with aqueous saturated sodium chloride solution, dried over magnesium sulfate, filtered and concentrated to give a pale yellow solid. Recrystallization of the solid from hexane gave pale yellow crystals melting at about 92°-95° C. and this was primarily 5-bromo-2-methoxypyridine-3-carboxaldehyde. The NMR spectrum showed the presence of the other possible aldehyde isomer (3-bromo-2-methoxypyridine-5-carboxaldehyde) but the ratio of the two isomers was about 12:1.

When the above procedure was repeated using 3-bromo-5-chloro-2-methoxypyridine, the product obtained was 5-chloro-2-methoxypyridine-3-carboxaldehyde melting at about 93°-96° C.

EXAMPLE 7

To a solution of 6.5 g of 5-bromo-2-methoxypyridine-3-carboxaldehyde in 30 ml of tetrahydrofuran under nitrogen was added 200 ml of methanol followed by 4.6 g of 4-chloroacetophenone. Then, a solution of 6.6 g of 85% potassium hydroxide in 15 ml of water was added. The mixture warmed, became yellow, and deposited a thick precipitate. It was then stirred mechanically for about 1.5 hours until the temperature fell back to about 25° C. It was then further cooled in an ice bath and neutralized by the addition of 20 ml of aqueous 5M hydrochloric aid in small portions. The resulting pasty mixture was poured into 400 ml of water, acidified to a pH of 1 with aqueous 1N hydrochloric acid and then filtered. The moist product was boiled with 2-propanol/ethyl acetate (3:1), cooled and filtered. The filter cake was dried under reduced pressure to give (E)-3-(5-bromo-2-methoxy-3-pyridinyl)-1-(4-chlorophenyl)-2-propen-1-one as a pale yellow solid melting at about 168.5°-171.5° C.

When the above procedure was repeated using 4-methylacetophenone, the product obtained was (E)-3-(5-bromo-2-methoxy-3-pyridinyl)-1-(4-methylphenyl)-2-propen-1-one.

Similarly, when 3,4-dichloroacetophenone was used in place of 4-chloroacetophenone in the above procedure, the product obtained was (E)-3-(5-bromo-2-methoxy-3-pyridinyl)-1-(3,4-dichlorophenyl)-2-propen-1-one.

EXAMPLE 8

A stirred solution of 65.9 g of (E)-5-bromo-α[2-(3,4-dichlorophenyl)ethenyl]-2-methoxy-3-pyridinemethanol in 600 ml of acetic acid was heated to 100° C. under nitrogen to give a mixture of allylic acetates and starting material. Then, 60 ml of 48% aqueous hydrobromic acid was added all at once and the progress of the reaction was monitored by thin layer chromatography while the temperature was maintained at 95°-100° C. After no more than 15 minutes, the mixture was cooled rapidly to 20° C. in an ice-water bath and then poured into 2 liters of water. Ether (1 liter) was used to extract the aqueous mixture. The ether layer was washed with three 1000-ml portions of water and then with aqueous saturated sodium bicarbonate solution, and finally with aqueous saturated sodium chloride solution. After drying over magnesium sulfate, and ether solution was filtered and concentrated under reduced pressure to give about 60 g of dark yellow solid. This crude product was purified by dissolving it in methylene chloride and filtering the solution through silica gel to give, after evaporation of the solvent, a colorless solid. This was then recrystallized from absolute ethanol to give 6-bromo-2-(3,4-dichlorophenyl)-2H-pyrano[2,3-b]pyridine melting at about 100.5°–101° C.

When the above procedure was repeated using the appropriately substituted starting materials, the following were obtained:

6-Bromo-2-phenyl-2H-pyrano[2,3-b]pyridine melting at about 103.5°–105° C.

6-Chloro-2-(3,4-dichlorophenyl)-2H-pyrano[2,3-b]pyridine.

6-Chloro-2-(4-chlorophenyl)-2H-pyrano[2,3-b]pyridine melting at about 91.5°–93° C.

EXAMPLE 9

The procedure of Example 5, paragraph 1 is repeated using 2-methyl-3-phenyl-2-propenal and 4-phenylbut-3-en-2-one in place of the 3,4-dichlorocinnamaldehyde to give the corresponding pyridinemethanol product. This is then reacted with acetic acid followed by hydrobromic acid according to the procedure of Example 8 to give the following products:

6-Bromo-3-methyl-2-phenyl-2H-pyrano[2,3-b]pyridine.
6-Bromo-4-methyl-2-phenyl-2H-pyrano[2,3-b]pyridine.

EXAMPLE 10

To a stirred suspension of 30 g of (E)-3-(5-bromo-2-methoxy-3-pyridinyl)-1-(3,4-dichlorophenyl)-2-propen-1-one in 275 ml of tetrahydrofuran and 260 ml of absolute ethanol was added 6.0 g of sodium borohydride. After 1 hour under nitrogen, the reaction mixture was partitioned between aqueous 1N sodium hydroxide solution and ether. The ether layer was washed with aqueous saturated sodium chloride solution, dried over sodium sulfate and concentrated under reduced pressure to give a pale yellow oil which was crude α-[2-(5-bromo-2-methoxy-3-pyridinyl)ethenyl]-3,4-dichlorobenzenemethanol. To a stirred solution of 25.9 g of this crude alcohol in 400 ml of acetic acid under nitrogen there was added 25 ml of 48% aqueous hydrobromic acid. The mixture was heated to 85° C. for about 30 minutes then cooled rapidly to 23° C. in an ice bath, and partitioned between water and ether. The ether layer was washed several times with water and then successively with aqueous saturated sodium bicarbonate and sodium chloride solutions. It was then dried over sodium sulfate and the solvent evaporated under reduced pressure to give a pale yellow oil. Filtration through a layer of silica gel using chloroform as eluant gave 6-bromo-2-(3,4-dichlorophenyl)-2H-pyrano[2,3-b]pyridine as a pale yellow solid which exhibited the same characteristics as the material obtained in Example 8.

When the above procedure was repeated starting with (E)-3-(5-bromo-2-methoxy-3-pyridinyl)-1-(4-methylphenyl)-2-propen-1-one, the product obtained was 6-bromo-2-(4-methylphenyl)-2H-pyrano[2,3-b]pyridine.

Similarly, when (E)-3-(5-bromo-2-methoxy-3-pyridinyl)-1-(4-chlorophenyl)-2-propen-1-one was used as the starting material, the product obtained was 6-bromo-2-(4-chlorophenyl)-2H-pyrano[2,3-b]pyridine.

EXAMPLE 11

To a solution of 2.9 g of 6-bromo-2-(3,4-dichlorophenyl)-2H-pyrano[2,3-b]pyridine in 40 ml of tetrahydrofuran was added 0.5 ml of 1,8-diazabicyclo[5.4.0]undec-7-ene. After 1 hour at 25° C., the reaction mixture was partitioned between ethyl acetate and aqueous saturated ammonium chloride solution. The ethyl acetate layer was dried over magnesium sulfate and the solvent was evaporated to leave a solid residue. This was recrystallized from ethanol to give 6-bromo-2-(3,4-dichlorophenyl)-4H-pyrano[2,3-b]pyridine melting at about 138°–139.5° C.

EXAMPLE 12

To a solution of 49.3 g of 6-bromo-2-(3,4-dichlorophenyl)-2H-pyrano[2,3-b]pyridine in 220 ml of anhydrous tetrahydrofuran was added 550 ml of absolute ethanol. The flask containing the solution was flushed with nitrogen and 60.4 g of an aqueous slurry of W-2 Raney Nickel was added. The mixture was then rapidly stirred under a hydrogen atmosphere for a total of 6 hours. Progress of the reaction was monitored by color spot test because the starting material and product could not be separated by thin layer chromatography (tlc). Thus, aliquots were periodically withdrawn by syringe and spotted on a tlc plate and developed in 15% ethyl acetate/hexane. The plate was dipped into a 1% solution of p-toluenesulfonic acid in ethanol, wiped dry and heated on a hot plate for several minutes. The olefinic starting material produces a dark yellow-brown spot and when the color spot test gave only a faint yellow discoloration, the reaction was judged to be complete. The hydrogen atmosphere was then replaced by nitrogen and the catalyst was filtered off through a pad of Celite. The catalyst was washed thoroughly with methylene chloride while taking care to keep it covered with solvent. The filtrate was concentrated under reduced pressure to a small volume and the crystals which formed were separated by filtration. The filtrate was then concentrated and flash chromatographed to give additional solid product. Recrystallization of the solid from ethanol gave 6-bromo-2-(3,4-dichloroophenyl)-3,4-dihydro-2H-pyrano[2,3-b]pyridine melting at about 106°–109° C. This compound has the following structural formula:

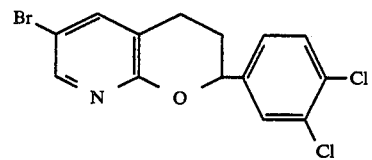

EXAMPLE 13

When the hydrogenation of Example 12 was repeated using the appropriate starting materials, the following compounds were obtained:

6-Chloro-2-(4-chlorophenyl)-3,4-dihydro-2H-pyrano[2,3-b]pyridine melting at about 109°–111° C.

6-Chloro-2-(3,4-dichlorophenyl)-3,4-dihydro-2H-pyrano[2,3-b]pyridine melting at about 106.5°–107.5° C.

6-Bromo-3,4-dihydro-2-phenyl-2H-pyrano[2,3-b]pyridine melting at about 109°–111° C.

6-Bromo-3,4-dihydro-2-(4-methylphenyl)-2H-pyrano[2,3-b]pyridine melting at about 126°–127° C.

6-Bromo-2-(4-chlorophenyl)-3,4-dihydro-2H-pyrano[2,3-b]pyridine melting at about 112.5°–114° C.

EXAMPLE 14

5-Bromo-2-methoxypyridine-3-carboxaldehyde is reacted with the appropriate acetophenone according to the procedure of Example 7. The resulting ketone is then reduced to the corresponding alcohol and cyclized according to the procedure described in Example 9. The unsaturated cyclization product is then hydrogenated according to the procedure of Example 12. In this way, the following compounds are obtained:
6-Bromo-2-(4-bromophenyl)-3,4-dihydro-2H-pyrano[2,3-b]pyridine.
6-Bromo-2-(3-chlorophenyl)-3,4-dihydro-2H-pyrano[2,3-b]pyridine.
6-Bromo-3,4-dihydro-2-(4-fluorophenyl)-2H-pyrano[2,3-b]pyridine.
6-Bromo-3,4-dihydro-2-(2,4,5-trichlorophenyl)-2H-pyrano[2,3-b]pyridine.

EXAMPLE 15

A suspension was prepared from 23.5 g of 2,5-bis(methylsulfonyl)pyridine and 200 ml of methanol and this was stirred rapidly under nitrogen while 24 ml of 25% sodium methoxide/methanol was added. This mixture was warmed to 50° C. for 20 minutes to give a homogeneous black solution. The solvent was removed by evaporation under reduced pressure and the resulting slurry was partitioned between ethyl acetate and water. The ethyl acetate layer was washed with aqueous saturated sodium chloride solution and dried over magnesium sulfate. The mixture was treated with carbon and filtered through Celite to give a pale yellow filtrate. Concentration of the filtrate under reduced pressure gave a pale yellow oil which solidified on cooling. This was recrystallized from 2-propanol to give 2-methoxy-5-(methylsulfonyl)pyridine as colorless crystals melting at about 85°–86.5° C. Bromination of this compound according to the procedure described in Example 2 gave 3-bromo-2-methoxy-5-(methylsulfonyl)pyridine melting at about 148.5°–150.5° C.

EXAMPLE 16

A mixture of 2.7 g of 3-bromo-2-methoxy-5-(methylsulfonyl)pyridine, 3.1 g of α-ethenyl-3,4-dichlorobenzenemethanol, 1.3 g of sodium bicarbonate, 10 ml of dimethylformamide and 0.11 g of palladium diacetate was stirred under nitrogen and heated to 120° C. After 6 hours, thin layer chromatography showed no unreacted bromopyridine starting material. The mixture was then cooled, diluted with ethyl acetate and filtered through Celite. The ethyl acetate solution was washed with water and then twice with aqueous saturated sodium chloride solution and dried over magnesium sulfate. The solution was then filtered and concentrated to a black oil. Excess alcohol was removed by Kugelrohr distillation and the glassy residue was taken up in methylene chloride and chromatographed on silica gel to give a pale yellow solid. This was recrystallized from ethanol/ethyl acetate to give 3-[2-methoxy-5-(methylsulfonyl)-3-pyridinyl]-1-(3,4-dichlorophenyl)propan-1-one melting at about 145°–146° C.

When 3-bromo-5-chloro-2-methoxypyridine was reacted with α-ethenyl-3,4-dichlorobenzenemethanol according to the above procedure, the product obtained was 3-(5-chloro-2-methoxy-3-pyridinyl)-1-(3,4-dichlorophenyl)propan-1-one melting at about 81°–82.5° C.

EXAMPLE 17

A solution of 0.35 g of 3-(5-chloro-2-methoxy-3-pyridinyl)-1-(3,4-dichlorophenyl)propan-1-one in 4 ml of tetrahydrofuran was added to a rapidly stirred suspension of 0.05 g of sodium borohydride in 4 ml of absolute ethanol. After 5 minutes, thin layer chromatography showed complete conversion of the starting material. The reaction mixture was then partitioned between ether and water and the ether layer was washed with aqueous saturated sodium chloride solution, dried over potassium carbonate and concentrated to give a colorless oil which later solidified. This product, 3-(5-chloro-2-methoxy-3-pyridinyl)-1-(3,4-dichlorophenyl)-propan-1-ol (0.32 g), was dissolved in 4 ml of acetic acid and heated to 100° C. under nitrogen. Then, 0.5 ml of 48% aqueous hydrobromic acid was added and heating was continued for 3 hours. The cooled reaction mixture was then partitioned between ether and water and the ether layer was extracted twice with aqueous saturated sodium bicarbonate, dried over magnesium sulfate and concentrated to give a colorless oil which later solidified. The product obtained in this way was 6-chloro-2-(3,4-dichlorophenyl)-3,4-dihydro-2H-pyrano[2,3-b]pyridine which was identical with the material prepared as described in Example 13.

When the above procedure was repeated using 3-[2-methoxy-5-(methylsulfonyl)-3-pyridinyl]-1-(3,4-dichlorophenyl)propan-1-one, the product obtained was 2-(3,4-dichlorophenyl)-3,4-dihydro-6-(methylsulfonyl)-2H-pyrano[2,3-b]pyridine melting at about 171.5°–173° C.

EXAMPLE 18

3-Bromo-2-methoxy-5-(methylsulfonyl)pyridine is reacted with the appropriate substituted α-ethenylbenzenemethanol according to the procedure of Example 16. The resulting ketone was then reduced to the corresponding alcohol by means of sodium borohydride and the alcohol was treated with hydrobromic acid to bring about cyclization, both as described in Example 17. In this way, the following compounds are obtained.
3,4-Dihydro-2-(4-methoxyphenyl)-6-(methylsulfonyl)-2H-pyrano[2,3-b]pyridine.
3,4-Dihydro-2-(3,4-methylenedioxyphenyl)-6-(methylsulfonyl)-2H-pyrano[2,3-b]pyridine.
3,4-Dihydro-6-(methylsulfonyl)-2-(3-phenoxyphenyl)-2H-pyrano[2,3-b]pyridine.

EXAMPLE 19

A suspension of 11.75 g of 2,5-bis(methylsulfonyl)-pyridine in 100 ml of 20% sulfuric acid was refluxed for 2.5 hours. Thin layer chromatography showed complete conversion to the corresponding 2-pyridinone. Then, 14.9 g of potassium iodate was added carefully to the rapidly stirred reaction mixture while the temperature was maintained at about 90°–100° C. An exothermic reaction took place with liberation of iodine. After 30 minutes, 8.0 g of potassium iodide in 20 ml of water was added dropwise over 1.5 hours. A thick precipitate developed during this addition. This mixture was allowed to cool to 25° C. and it was diluted to 200 ml with water and filtered to collect the precipitate. This precipitate was washed sequentially with water, aqueous 5% sodium bisulfite solution, again with water and finally twice with anhydrous ethanol. It was then dried in vacuo to give 3-iodo-5-(methylsulfonyl)-2(1H)-pyridinone as pale brown crystals melting at about 273°–276° C. with decomposition.

EXAMPLE 20

A suspension of 9.0 g of 3-iodo-5-(methylsulfonyl)-2(1H)-pyridinone in 30 ml of phosphorus oxychloride was refluxed under nitrogen for 4 hours and gave a homogeneous mixture. This solidified on cooling and unreacted phosphorus oxychloride was removed under reduced pressure. The resulting white solid residue was dissolved in methylene chloride and extracted first with water and twice with aqueous 1N sodium hydroxide solution. The mixture was shaken until the aqueous phase remained basic. The methylene chloride solution was then dried over magnesium sulfate and concentrated to leave a white solid residue. This was recrystallized from ethyl acetate/hexane to give 2-chloro-3-iodo-5-(methylsulfonyl)pyridine as colorless needles melting at about 178.5°–180.5° C.

EXAMPLE 21

A mixture of 0.95 g of 2-chloro-3-iodo-5-(methylsulfonyl)pyridine, 0.91 g of α-ethenyl-3,4-dichlorobenzenemethanol, 0.77 g of N,N-diisopropylethylamine, 0.04 g of tri-o-tolyphosphine, 0.02 g of palladium diacetate and 3 ml of dimethylformamide was heated to 100° C. under nitrogen. The mixture was heated at this temperature for 20 minutes and then at 116° C. for an additional 20 minutes at which point thin layer chromatography showed no iodopyridine starting material. The mixture was then cooled and partitioned between 1N hydrochloric acid and methyl acetate. The ethyl acetate layer was washed twice with aqueous saturated sodium chloride solution, dried over magnesium sulfate and filtered and the filtrate was concentrated to a dark solid residue. Column chromatography of this residue (silica gel, 1:1 ethyl acetate/hexane) gave a pale yellow solid. This was recrystallized from ethanol/ethyl acetate to give 3-[2-chloro-5-(methylsulfonyl)-3-pyridinyl]-1-(3,4-dichlorophenyl)propan-1-one melting at about 128.5°–130.5° C.

EXAMPLE 22

A solution of 0.39 g of 3-[2-chloro-5-(methylsulfonyl)-3-pyridinyl]-1-(3,4-dichlorophenyl)propan-1-one in 15 ml of methylene chloride was cooled to −70° C. under nitrogen and then a solution of 1.0 ml of 1.5M diisobutylaluminum hydride/toluene was added dropwise over 3 minutes while keeping the temperature below −65° C. After an additional 5 minutes, the mixture was quenched by careful addition of 1.5 ml of a mixture consisting of 10% water, 40% acetic acid and 50% ether. The reaction mixture was then allowed to warm to 0° C. and was partitioned between water and methylene chloride. The methylene chloride layer was washed with aqueous saturated sodium bicarbonate solution, dried over magnesium sulfate and filtered, and the filtrate was concentrated to a colorless solid, 3-[2-chloro-5-(methylsulfonyl)-3-pyridinyl]-1-(3,4-dichlorophenyl)propan-1-ol. This solid was dissolved in 2 ml of anhydrous dimethyl sulfoxide and added to a stirred suspension of 0.07 g of 50% sodium hydride (previously freed of oil by washing with hexane) in 10 ml of dimethyl sulfoxide under nitrogen. Gas evolution took place and the mixture first became lavender and then cherry red. After 15 minutes, it was partitioned between ethyl acetate and 1N hydrochloric acid. The yellow ethyl acetate layer was washed with water and then twice with aqueous saturated sodium chloride solution, dried over magnesium sulfate and filtered and the filtrate was concentrated to leave a pale yellow solid. This solid was recrystallized from a mixture of 2-propanol and ethyl acetate to give 2-(3,4-dichlorophenyl)-3,4-dihydro-6-(methylsulfonyl)-2H-pyrano[2,3-b]pyridine melting at about 171.5°–172.5° C. This material exhibited the same spectral characteristics as the material prepared by the procedure described in Example 17. This compound has the following structural formula:

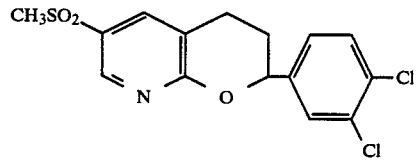

EXAMPLE 23

A solution of 3.6 g of 6-bromo-2-(3,4-dichlorophenyl)-3,4-dihydro-2H-pyrano[2,3-b]pyridine in a mixture of 50 ml of toluene and 25 ml of anhydrous ether was cooled to −100° C. under nitrogen and 3.8 ml of 2.9M tert-butyllithium/pentane was added dropwise over about 5 minutes while keeping the temperature below −100° C. This gave a deep blue-green mixture containing the lithio intermediate (i.e., lithium replacing the bromine in the starting material). After 20 minutes, 1.8 ml of dimethyldisulfide was added. The mixture was then allowed to warm to 0° C. and it was partitioned between ether and water. The ether layer was washed with aqueous saturated sodium chloride solution, dried over potassium carbonate and concentrated to a yellow oil which solidified on cooling. Column chromatography on silica gel (20% ethyl acetate/hexane) gave pure product which was further recrystallized from hexane/ethyl acetate to give 2-(3,4-dichlorophenyl)-3,4-dihydro-6-(methylthio)-2H-pyrano[2,3-b]pyridine as colorless needles melting at about 109°–111° C.

When the above procedure was repeated using the appropriate starting bromo compounds, the following compounds were obtained:

2-(4-Chlorophenyl)-3,4-dihydro-6-(methylthio)-2H-pyrano[2,3-b]pyridine melting at about 103°–105° C.

3,4-Dihydro-6-(methylthio)-2-phenyl-2H-pyrano[2,3-b]pyridine melting at about 105°–107° C.

EXAMPLE 24

6-Bromo-2-(3,4-dichlorophenyl)-3,4-dihydro-2H-pyrano[2,3-b]pyridine (1.5 g) was converted to the lithio intermediate by the procedure described in Example 23 and then quenched at −85° C. with excess methanol. Chromatographic purification of the crude product gave 2-(3,4-dichlorophenyl)-3,4-dihydro-2H-pyrano[2,3-b]pyridine as a cream colored solid melting at about 99°–100° C.

EXAMPLE 25

6-Bromo-2-(3,4-dichlorophenyl)-3,4-dihydro-2H-pyrano[2,3-b]pyridine (0.85 g) was converted to the lithio intermediate by the procedure described in Example 23 and then quenched at −95° C. with excess n-butyl disulfide. Chromatographic purification of the crude product gave a powdery while solid which was further recrystallized from ethyl acetate/hexane to give 6-(n-butylthio)-2-(3,4-dichlorophenyl)-3,4-dihydro-2H-pyrano[2,3-b]pyridine melting at about 59.5–61° C.

EXAMPLE 26

6-Bromo-2-(3,4-dichlorophenyl)-3,4-dihydro-2H-pyrano[2,3-b]pyridine (1.3 g) was converted to the corresponding lithio intermediate by the procedure described in Example 23 and this was quenched at −100° C. with a solution of 0.8 g of benzonitrile in 4 ml of toluene. Crude product was isolated by the procedure described in Example 23 and it was purified by chromatography (silica gel, 2:1 hexane/ethyl acetate) to give 6-benzoyl-2-(3,4-dichlorophenyl)-3,4-dihydro-2H-pyrano[2,3-b]pyridine melting at about 155°–158° C.

EXAMPLE 27

6-Bromo-2-(3,4-dichlorophenyl)-3,4-dihydro-2H-pyrano[2,3-b]pyridine (1.5 g) was converted to the corresponding lithio intermediate according to the procedure described in Example 23 and then quenched at −90° C. with 1.3 ml of tri-n-butyl borate. The resulting dark solution was stirred at −75° C. for 2 hours and then allowed to warm to 0° C. The mixture was then acidified with 3N hydrochloric acid, the organic phase was separated, and the aqueous layer was extracted with ether. The combined organic layers were concentrated to give a light brown, tacky solid. To this material was added 25 ml of 30% hydrogen peroxide and the resulting mixture was warmed at 60° C. for 30 minutes. The mixture was then cooled and diluted with 75 ml of water and the resulting mixture was extracted with two 50-ml portions of methylene chloride. The methylene chloride extracts were combined, washed with aqueous saturated sodium chloride solution, dried over sodium sulfate and concentrated to give a yellow solid. Column chromatography (silica gel, 3% ethyl acetate/hexane) gave 2-(3,4-dichlorophenyl)-3,4-dihydro-6-hydroxy-2H-pyrano[2,3-b]pyridine melting at about 218°–219° C.

EXAMPLE 28

6-Bromo-2-(3,4-dichlorophenyl)-3,4-dihydro-2H-pyrano[2,3-b]pyridine (14.4 g) in a mixture of 400 ml of toluene and 200 ml of ether was converted to the corresponding lithio intermediate by the procedure described in Example 23. The lithio intermediate, at −100° C., was quenched by the addition of 10.8 ml of methyl disulfide. The mixture was then allowed to warm to −50° C. and it was partitioned between water and ether. The aqueous layer was extracted with ether and the combined organic layers were washed with aqueous saturated sodium chloride solution, dried over potassium carbonate and filtered and the filtrate was concentrated in vacuo to give a dark yellow oil which later solidified. The crude thioether obtained in this way was dissolved in 80 ml of tetrahydrofuran, diluted with 160 ml of methanol, and cooled in an ice-water bath while a solution of 49.2 g of potassium peroxymonsulfuric acid in 150 ml of water was added at a rate so that the temperature remained below 30° C. A thick white precipitate developed and efficient mechanical stirring was necessary. After 3 hours, the mixture was poured into 1 liter of water and extracted with ethyl acetate. The aqueous layer was extracted with additional ethyl acetate and the combined organic layers were washed with aqueous saturated sodium chloride solution, dried over magnesium sulfate and filtered and the filtrate concentrated to give a yellow solid. This solid was recrystallized from a mixture of 2-propanol and ethyl acetate to give 2-(3,4-dichlorophenyl)-3,4-dihydro-6-(methylsulfonyl)-2H-pyrano[2,3-b]pyridine melting at about 172°–173.5° C. This product was identical in all respects with the material prepared by other procedures in the previous examples.

When the above procedure was repeated using the appropriate starting materials, the following compounds were obtained:
2-(4-Chlorophenyl)-3,4-dihydro-6-(methylsulfonyl)-2H-pyrano[2,3-b]pyridine melting at about 187°–189° C.
3,4-Dihydro-6-(methylsulfonyl)-2-phenyl-2H-pyrano[2,3-b]pyridine melting at about 188°–189° C.

EXAMPLE 29

To a stirred solution of 1.0 g of 2-(3,4-dichlorophenyl)-3,4-dihydro-6-(methylthio)-2H-pyrano[2,3-b]pyridine in 25 ml of methylene chloride at −25° C. there was added dropwise a solution of 0.55 g of 80–85% m-chloroperoxybenzoic acid in 20 ml of methylene chloride over 5–10 minutes while keeping the temperature between −20° and −30° C. A precipitate formed. The mixture was then allowed to warm to −5° C. over 2 hours and then extracted with aqueous saturated sodium bicarbonate solution, aqueous saturated sodium chloride solution, dried over sodium sulfate and concentrated under reduced pressure to leave a pale yellow solid. This was recrystallized from a mixture of ethyl acetate and hexane to give 2-(3,4-dichlorophenyl)-3,4-dihydro-6-(methylsulfinyl)-2H-pyrano[2,3-b]pyridine as a cream-colored solid melting at about 159°–162° C.

EXAMPLE 30

To a stirred solution of 1.9 g of 3-(5-chloro-2-methoxy-3-pyridinyl)-1-(3,4-dichlorophenyl)propan-1-one in 55 ml of anhydrous tetrahydrofuran at 5° C. under nitrogen there was added, via syringe, 2.6 ml of 2.9M methylmagnesium chloride/tetrahydrofuran over a period of about 10 minutes. The resulting yellow mixture was allowed to warm to 23° C. and, after 2 hours, was quenched by careful addition of 20 ml of 0.05N hydrochloric acid. The mixture was then poured into 50 ml of water and extracted twice with ether. The combined extracts were washed with water and saturated aqueous sodium chloride solution and then dried over sodium sulfate. The solvent was then evaporated under reduced pressure to leave a yellow oil with spectra expected for the alcohol. To a solution of 1.15 g of this alcohol in 25 ml of acetic acid under nitrogen there was added 1.2 ml of 48% hydrobromic acid. The solution was then stirred and warmed to 100° C. After 10 minutes, the mixture was cooled to 25° C. and partitioned between ether and water. The ether layer was washed with aqueous saturated sodium bicarbonate solution (twice), and then saturated aqueous sodium chloride solution, dried over sodium sulfate and concentrated to give a viscous orange oil. This was subjected to column chromatography (silica gel, 5% ethyl acetate/hexane initially, then 7% ethyl acetate/hexane, and finally with 1:1 ethyl acetate/hexane). The lower $r_f$ fraction was then further subjected to preparative thin layer chromatography (15% ethyl acetate/hexane) to give a colorless oil. This was further triturated with hexane to give, after removal of supernatant, a while granular solid melting at about 83°–84° C. which was 6-chloro-2-(3,4-dichlorophenyl)-3,4-dihydro-2-methyl-2H-pyrano[2,3-b]pyridine.

What is claimed is:

1. A compound of the formula

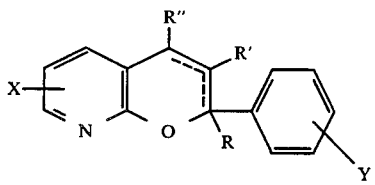

wherein R, R' and R" are each hydrogen or lower alkyl of 1–4 carbon atoms; X is chloro, bromo, alkylthio, alkylsulfinyl, alkylsulfonyl, hydroxy, alkoxy, benzoyl, acetyl or alkyl; Y is halo, di- or tri-chloro, alkyl, alkoxy, methylenedioxy, or phenoxy; the dotted line indicates the optional presence of a double bond at the 2,3- or 3,4-positions; with the proviso that when the dotted line represents a double bond at the 2,3-position then the R-group is not present.

2. A compound the formula

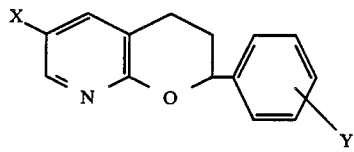

wherein X is hydrogen, chloro, bromo, alkylthio, alkylsulfinyl, alkylsulfonyl, hydroxy, alkoxy, benzoyl, acetyl or alkyl; and Y is hydrogen, halo, di- or tri-chloro, alkyl, alkoxy, methylenedioxy, or phenoxy.

3. A compound according to claim 1 which has the formula

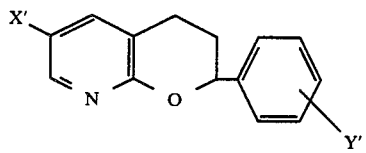

wherein X' is chloro, bromo, alkylthio, alkylsulfinyl, alkylsulfonyl, hydroxy, alkoxy, benzoyl, acetyl or alkyl; and Y' is halo, di- or tri-chloro, alkyl, alkoxy, methylenedioxy or phenoxy.

4. A compound according to claim 1 which has the formula

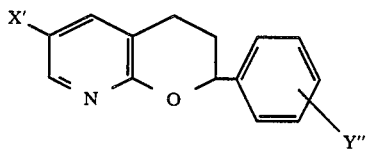

wherein X' is chloro, bromo, alkylthio, alkylsulfinyl, alkylsulfonyl, hydroxy, alkoxy, benzoyl, acetyl or alkyl; and Y" is chloro or di-chloro.

5. A compound according to claim 1 which has the formula

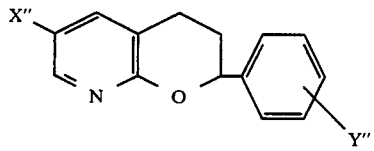

wherein X" is chloro, bromo or methylsulfonyl; and Y" is chloro or di-chloro.

6. A compound according to claim 1 which has the formula

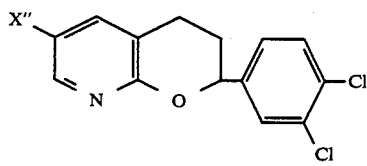

wherein X" is chloro, bromo or methylsulfonyl.

7. A compound according to claim 1 which is 6-bromo-2-(3,4-dichlorophenyl)-3,4-dihydro-2H-pyrano[2,3-b]pyridine.

8. A compound according to claim 1 which is 6-chloro-2-(3,4-dichlorophenyl)-3,4-dihydro-2H-pyrano[2,3-b]pyridine.

9. A compound according to claim 1 which is 2-(3,4-dichlorophenyl)-3,4-dihydro-6-(methylsulfonyl)-2H-pyrano[2,3-b]pyridine.

10. A compound according to claim 1 which is 6-bromo-2-(4-chlorophenyl)-3,4-dihydro-2H-pyrano[2,3-b]pyridine.

11. A compound according to claim 1 which is 6-chloro-2-(4-chlorophenyl)-3,4-dihydro-2H-pyrano[2,3-b]pyridine.

12. A compound according to claim 1 which is 2-(4-chlorophenyl)-3,4-dihydro-6-(methylsulfonyl)-2H-pyrano[2,3-b]pyridine.

13. A compound according to claim 1 which is 2-(3,4-dichlorophenyl)-3,4-dihydro-6-(methylthio)-2H-pyrano[2,3-b]pyridine.

14. A compound according to claim 1 which is 2-(3,4-dichlorophenyl)-3,4-dihydro-6-(methylsulfinyl)-2H-pyrano[2,3-b]pyridine.

15. A compound according to claim 1 which is 2-(4-chlorophenyl)-3,4-dihydro-6-(methylthio)-2H-pyrano[2,3-b]pyridine.

16. A method for inhibiting viruses which comprises contacting viruses or virus host cells with an effective virus inhibiting amount of a compound of the formula:

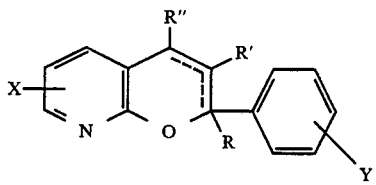

wherein R, R' and R" are each hydrogen or lower alkyl of 1–4 carbon atoms; X is hydrogen, chloro, bromo, alkylthio, alkylsulfinyl, alkylsulfonyl, hydroxy, alkoxy, benzoyl, acetyl or alkyl; Y is hydrogen, halo, di- or tri-chloro, alkyl, alkoxy, methylenedioxy, or phenoxy; the dotted line indicates the optional presence of a double bond at the 2,3- or 3,4-positions; with the proviso that when the dotted line represents a double bond at the 2,3-position then the R-group is not present.

* * * * *

UNITED STATES PATENT AND TRADEMARK OFFICE
CERTIFICATE OF CORRECTION

PATENT NO. : 4,588,733

DATED : May 13, 1986

INVENTOR(S) : Thomas M. Bargar and John K. Daniel

It is certified that error appears in the above-identified patent and that said Letters Patent are hereby corrected as shown below:

Column 2, line 30, in the structural formula,

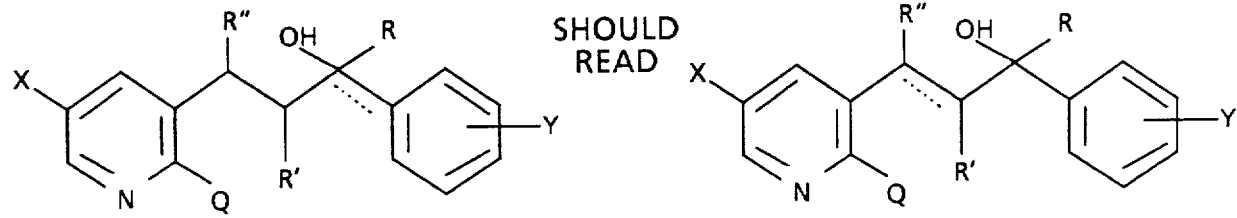

Column 12, line 38, "dichloroophenyl" should read -- dichlorophenyl --.

Column 17, line 57, "peroxymonsulfuric" should read -- peroxymonosulfuric --.

Column 19, line 23, Claim 2, "A compound the formula" should read -- A compound of the formula --.

Signed and Sealed this

Fourteenth Day of June, 1988

Attest:

DONALD J. QUIGG

Attesting Officer      Commissioner of Patents and Trademarks